United States Patent [19]

Faries, Jr. et al.

[11] Patent Number: 5,163,299

[45] Date of Patent: Nov. 17, 1992

[54] METHOD AND APPARATUS FOR PRODUCING STERILE SLUSH

[75] Inventors: Durward I. Faries, Jr., McLean, Va.; Bruce R. Heymann, Silver Spring, Md.

[73] Assignee: O.R. Solutions, Inc., Reston, Va.

[21] Appl. No.: 851,884

[22] Filed: Mar. 16, 1992

[51] Int. Cl.$^5$ .............................................. F25C 1/00
[52] U.S. Cl. ........................................ 62/66; 62/342; 128/846
[58] Field of Search ......................... 62/66, 340, 342; 4/DIG. 18, 452, 484, 580, 655; 128/846, 849; 165/63

[56] References Cited

U.S. PATENT DOCUMENTS 4,393,659 7/1983 Keyes et al. ........................... 62/66
4,934,152 6/1990 Templeton ............................. 62/66

Primary Examiner—William E. Tapolcai

[57] ABSTRACT

The system disclosed in U.S. Pat. No. 4,393,659 (Keyes et al) for producing surgical slush is improved to permit the slush to be collected directly in a drape or sheet, thereby eliminating the separate product basin and liquid thermal transfer medium required in the prior system. The sheet is made to conform to a heat transfer basin atop the system refrigeration unit and is impervious to the surgical liquid from which the slush is formed. In order to prevent damage to the drape by abrupt edges of basin spacers permanently projecting from the heat transfer wall into the basin interior, the spacers are covered or recessed by protective members eliminating all possible contact between the sheet and the spacer edges.

18 Claims, 2 Drawing Sheets

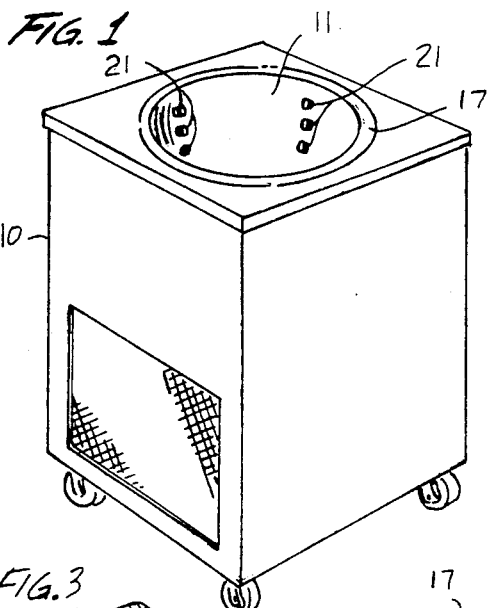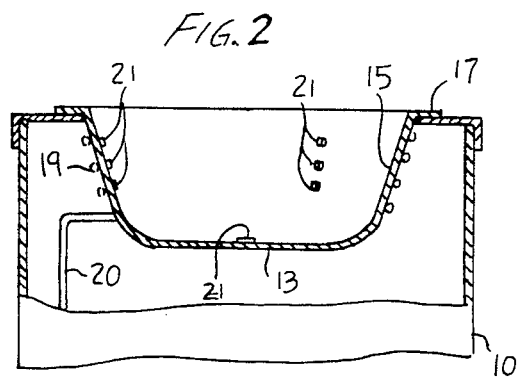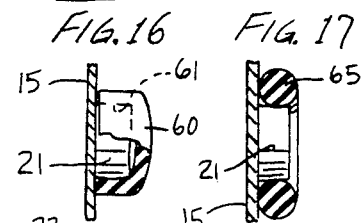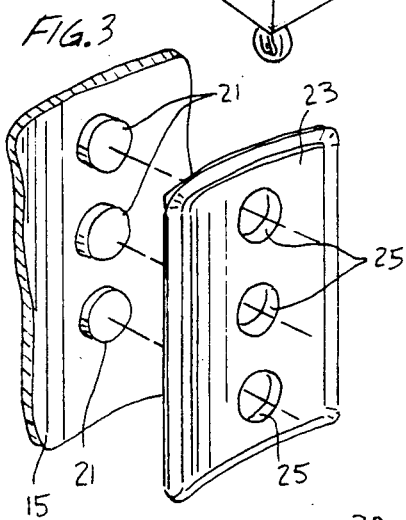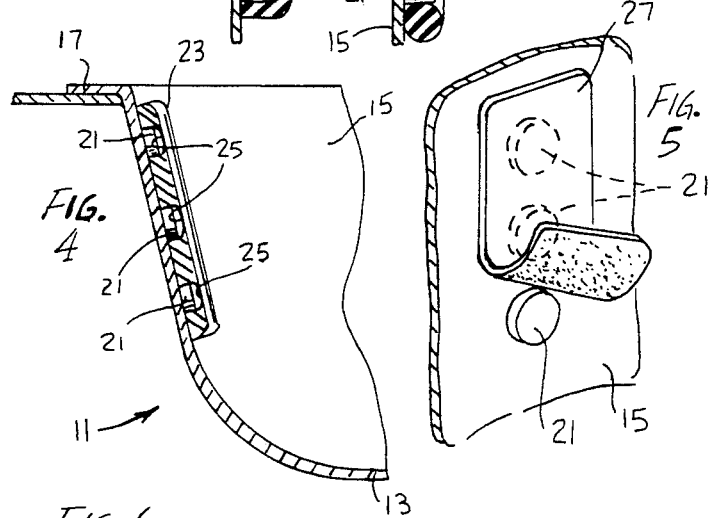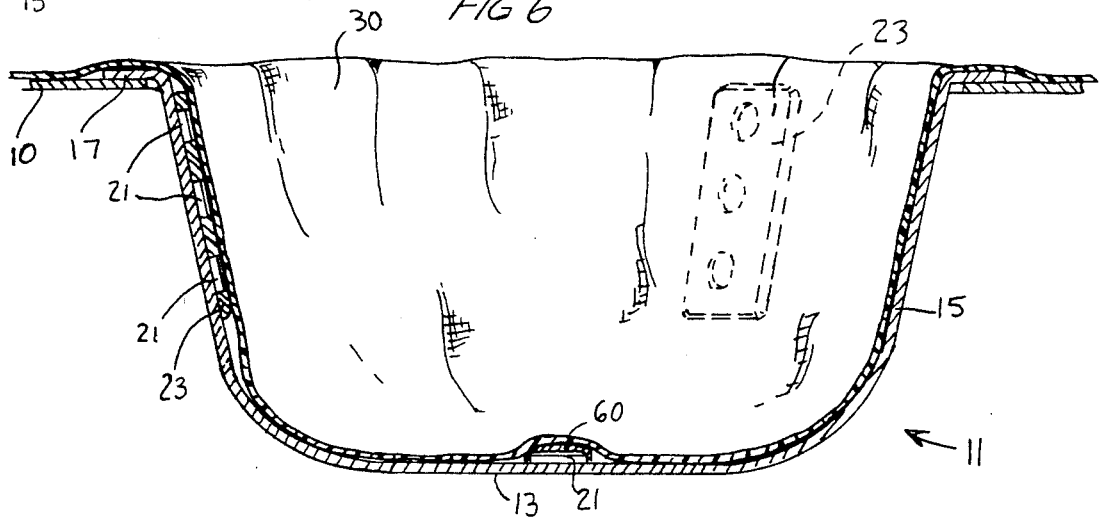

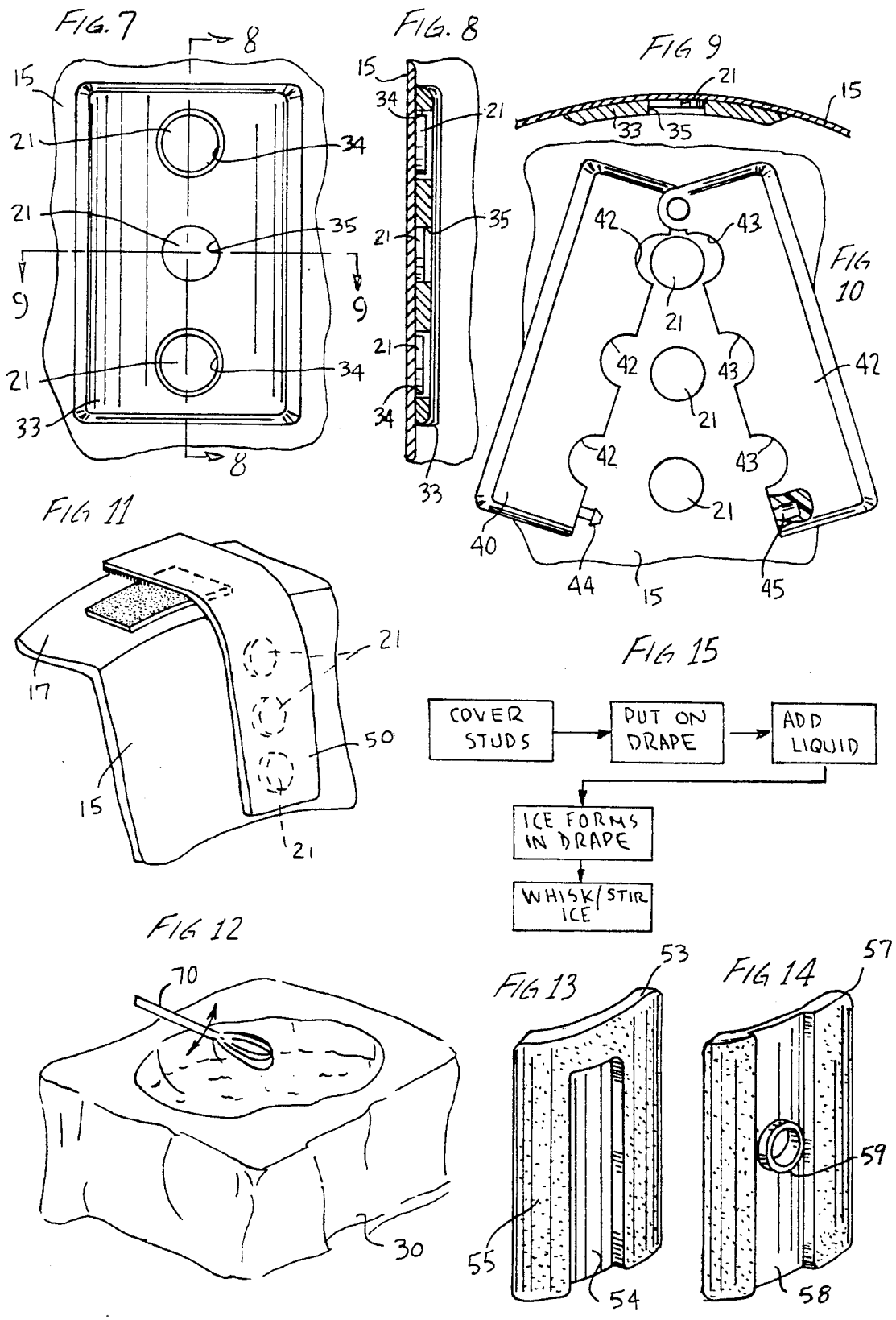

000# METHOD AND APPARATUS FOR PRODUCING STERILE SLUSH

BACKGROUND OF THE INVENTION

1. Technical Field

The present invention pertains to improvements in methods and apparatus for producing surgical sterile slush. In particular, the present invention is an improvement of the methods and apparatus disclosed in U.S. Pat. No. 4,393,659 (Keyes et al). The disclosure in that patent is expressly incorporated herein in its entirety by this reference.

2. Discussion Of The Prior Art

The Keyes et al patent discloses a surgical slush producing system having a cabinet with a heat transfer basin at its top. A refrigeration mechanism in the cabinet takes the form of a closed refrigeration loop including: an evaporator in heat exchange relation to the exterior of the heat transfer basin; a compressor; a condenser; and a refrigeration expansion control, all located in the cabinet. A separate product basin is configured to be removably received in the heat transfer basin. Spacers, in the form of short cylindrical stubs or buttons, are arranged in three groups spaced about the heat transfer basin and projecting into the heat transfer basin interior to maintain a prescribed space between the two basins. During use, that space contains a thermal transfer liquid such as alcohol or glycol serving as a thermal transfer medium between the two basins. A sterile sheet of material impervious to the thermal transfer medium is disposed between the product basin exterior and the liquid thermal transfer medium to preserve the sterile nature of the product basin. Surgically sterile liquid, such as sodium chloride solution, is placed in the product basin and congeals on the side of that basin when the refrigeration unit is activated. A scraping tool is utilized to scrape congealed sterile material from the product basin side to thereby form a slush of desired consistency in the product basin.

As noted in U.S. Pat. No. 4,934,152 (Templeton), the above-described system has a number of disadvantages. Specifically, the separate product basin must be removed and re-sterilized after each use. In addition, the glycol or other thermal transfer medium is typically highly flammable or toxic and, in any event, complicates the procedure. The Templeton patent discloses a solution to these problems by constructing an entirely new apparatus whereby the product basin is eliminated in favor of a sterilized drape impervious to the sterile surgical liquid, the drape being made to conform to the basin and directly receive the sterile liquid. Congealed liquid is scraped off the sides of the conformed drape receptacle to form the desired slush.

While the Templeton approach solves the aforesaid problems associated with the Keyes et al system, it requires the user to purchase an entirely new system. It is desirable that the aforementioned problems be addressed in the context of existing systems constructed in accordance with the Keyes et al patent. However, if one attempts to eliminate the product basin and the requirement for a thermal transfer medium from the Keyes et al system by merely using a drape as proposed by Templeton, more often than not the drape is ripped by the basin spacers projecting from the heat transfer basin. The spacers are permanently secured to the basin wall and include sharp or abrupt annular edges that tend to tear or snag or slice the drape, particularly during stirring.

OBJECTS AND SUMMARY OF THE INVENTION

It is therefore an object of the present invention to provide an improved method and apparatus for utilizing the Keyes et al surgical slush producing apparatus whereby to eliminate the above-described disadvantages. It is a more specific of the invention to modify the Keyes et al structure and apparatus to permit sterile slush to be formed directly in a surgical drape receptacle without danger of tearing or snagging the drape on the spacers present in the heat transfer basin.

In accordance with the present invention, the spacers in the heat transfer basin of the Keyes et al apparatus are protected so as to eliminate contact between their exposed edges and a liquid-receiving drape receptacle placed in and conforming to the basin. The spacers may be completely covered, individually or in groups, by protective members having no abrupt edges or corners. Alternatively, the spacers may be surrounded with a protective member projecting forwarding of the spacers so as to cause the spacer edges to be recessed relative to the protective member and inaccessible to the drape. A whisk, rather than a scraper, is employed to stir the congealed liquid in the basin-conforming drape to permit collection of slush at a desired consistency within the drape receptacle. The disposable drape may be removed and discarded after use.

BRIEF DESCRIPTION OF THE DRAWINGS

The above and still further objects, features and advantages of the present invention will be apparent upon consideration of the following detailed description of the specific embodiments thereof, particularly when taken in conjunction with the accompanying drawings wherein like reference numerals in the various figures are utilized to designate like components, and wherein:

FIG. 1 is a view in perspective of the prior art slush producing system that is modified pursuant to the present invention;

FIG. 2 is an elevational view in partial section of the transfer basin and basin spacers of the prior art system of FIG. 1;

FIG. 3 is an exploded view in perspective of the basin spacers of FIG. 1 and a protective device applied to the basin spacers in accordance with the present invention;

FIG. 4 is an elevational view in partial section of the protective device of FIG. 3 secured to the basin spacers in the system of FIG. 1;

FIG. 5 is a view in perspective of an alternative protective device of the present invention applied to the basin spacers;

FIG. 6 is an elevational view in partial section showing a drape receptacle conforming to the basin of FIG. 1 with a protective device secured to the basin spacers;

FIG. 7 is a front view in elevation of the protective device of FIG. 3;

FIG. 8 is an elevational view in section taken along lines 8—8 of FIG. 7;

FIG. 9 is a view in section taken along lines 9—9 of FIG. 7;

FIG. 10 is a partial view in elevation of another form of protective device of the present invention applied to basin spacers;

FIG. 11 is an exploded view in perspective of another embodiment of the protective device of the present invention secured to the basin of FIG. 1 to cover basin spacers;

FIG. 12 is a view in perspective of the apparatus of the present invention shown during a slush forming procedure;

FIG. 13 is a rear view in perspective of another embodiment of the protective device of the present invention;

FIG. 14 is a rear view in perspective of still another protective device embodiment of the present invention;

FIG. 15 is a functional block diagram illustrating the method of the present invention;

FIG. 16 is a side elevation view in partial section showing another protective device embodiment of the present invention; and FIG. 17 is a side view in elevation and partial section showing still another protective device embodiment of the present invention.

DESCRIPTION OF THE PREFERRED EMBODIMENTS

Referring in detail to FIGS. 1 and 2 of the drawings, a slush generating system of the type described and illustrated in U.S. Pat. No. 4,393,659 (Keyes et al) includes a cabinet 10 having a top surface with an opening in which a heat transfer basin 11 is mounted. Basin 11 is made of a thermally conductive material, typically stainless steel, and includes a generally flat bottom wall 13, an upwardly diverging frusto-conical side wall 15, and a top flange 17 directed radially outward and secured in overlying relation to the top surface of the cabinet. A refrigeration unit is mounted in cabinet 10, it being noted that only the evaporator 19 of the refrigeration unit is illustrated in FIG. 2. The refrigeration unit is conventional and includes a compressor, a condenser, and an expansion control unit connected by appropriate fluid conduit 20 in a closed refrigeration loop with evaporator 19. The evaporator is in the form of a coil wound about the exterior surface of basin 11 in thermal transfer relation therewith. When the refrigeration unit is activated (i.e., by means of appropriate controls, not shown), evaporator 19 cools the side wall 15 of basin 11 to substantially below the freezing temperature of the liquid to be used in forming the sterile surgical slush; this temperature is preferably on the order of 25° F. to 28° F. For further details of the structure and operation of the refrigeration unit, reference is made to the aforesaid Keyes et al patent.

As noted hereinabove, operation of the Keyes et al system involves supporting a second basin within basin 11 but in spaced relation to the walls of basin 11 so that a thermal transfer medium, such as glycol, can be disposed between the two basins. In order to effect the necessary spacing between the basins, basin 11 is provided with a plurality of spacers 21 projecting into the basin interior from side wall 15 and bottom wall 13. In a system marketed under the Keyes et al patent (e.g., model 20-12, manufactured by Taylor Company of Rockton, Ill.), spacers 21 are arranged in three groups spaced equiangularly (i.e., by 120°) about basin side wall 15, each group comprising three spacers separated in vertical alignment; one spacer 21 is centered on bottom wall 13. Each spacer 21 is made of the same material as basin 11 and takes the form of a short cylindrical stud or button having one end welded or otherwise secured to the basin wall 15; alternatively, the spacers may be formed integrally with the basin. In either case, the distal end of spacer 21 is a flat circular surface bordered by an abrupt or sharp annular edge where the circular surface intersects the cylindrical surface. As described hereinabove, that annular edge tends to tear or snag a sheet or drape if one attempts to conform the drape to the basin walls and directly collect and freeze surgical liquid in the drape.

Referring to FIGS. 3 and 4, in accordance with one embodiment of the present invention, an apertured plate 23 is provided to protect each group of side wall spacers against possible contact between the abrupt spacer edges and a drape conforming to the interior walls of basin 11. Each plate 23 has a generally rectangular configuration but is slightly arcuate rather than planar so as to match the contour of a short segment of frusto-conical side wall 15 of basin 11. More precisely, plate 23 has straight vertical edges with arcuate top and bottom horizontal edges so that the front surface of the plate appears concave between the vertical edges. Three vertically aligned holes 25 are defined entirely through plate 23 substantially midway between its vertical edges. Holes 25 are spaced and sized to permit them to fit over a respective group of spacers 21 when the convex rear surface of the plate is placed flush against the concave surface of basin side wall 15. With the plate thusly positioned, the forward surfaces of spacers 21 are either flush with or recessed from the front surface of the plate. Accordingly, the abrupt annular edges surrounding the front surfaces of the spacers are not accessible to contact a drape placed in the basin. In addition, the outer edges and corners of plate 23 are rounded to further assure that such a drape cannot be torn or snagged thereon.

Protective plate 23 may be secured in place in a number of ways, such as by placing adhesive material between the rear surface of the plate and the interior surface of basin side wall 15. Alternatively, one or more holes 25 may be sized to provide a force-fit onto one or more corresponding spacers so that the plate is securely held in place by frictional engagement. The plate may be made of metal or plastic (e.g., silicone) and may be rigid or resilient. In the preferred embodiment plate 25 is made of thermally conductive material to permit efficient thermal transfer therethrough.

An alternative protective member according to the present invention is illustrated in FIG. 5 and takes the form of a strip 27 of suitably thick fabric (e.g., canvas) employed for each group of spacers 21. Strip 27 is sized to entirely cover all three spacers 21 in a group and is not apertured as is plate 23. Instead, the softness of the fabric of strip 27 combines with the thickness of the strip to effectively blunt and smooth the abruptness of the annular edges of the spacers when viewed from the basin interior. Strip 27 is attached to the front surface of the spacers and to the surrounding area of basin side wall 15 by adhesive material preferably in the form of a backing on the rear surface of the strip.

FIG. 6 illustrates basin 11 with protective members 23 and overlaid with a drape 30 positioned to conform to the side wall 15 and bottom wall 13 of the basin. It is to be understood that the use of plate 23 in this illustration is representative only, and that all of the other protective members and devices disclosed herein can replace plate 23 for purposes of this description. Drape 30 serves as a receptacle for the sterile liquid (e.g., a 0.85% to 0.9% sodium chloride solution) to be converted to surgical slush. Drape 30 is made from a material that is impervious to the sterile liquid and sufficiently soft and flexible to conform to the basin walls.

The thickness of the drape is preferably minimized to render thermal transfer therethrough most efficient, yet the thickness is sufficient to resist tearing and puncturing of the drape during whisking of slush and other normal use. Typically, by way of example only, the drape is made of materials commonly used in hospitals for surgical drapes and has a thickness in the range of 4.5 to 6.0 mils. The drape 30 may also be made of the polyurethane film disclosed for the drape in the aforementioned Templeton patent. Drape 30 is designed to be disposable after a single use and is provided presterilized and prepackaged in a leak proof plastic bag or other sealed container that preserves the sterile nature of the drape during storage.

An alternative protective plate embodiment of the present invention is illustrated in FIGS. 7, 8 and 9. Plate 33 is identical to plate 23 in all respects except that central hole 35 in plate 33 has a slightly smaller diameter than the end holes 34. It sometimes occurs that all spacers 21 in a group are not exactly the same size, or that the spacers in a group are not precisely vertically aligned. In plate 33, the center hole 35 is configured to engage the central spacer 21 in a force fit to secure the plate to the basin. The larger holes 34 provide sufficient slack to accommodate any misalignment or mis-sizing of the other spacers.

Referring to FIG. 10, another approach to accommodating irregularly sized or aligned spacers 21 is to provide the protective plate in two plate halves 40 and 41 separable along a central axis dividing the spacer-receiving holes into two halves 42 and 43, respectively. The plates may be pivotably joined along one horizontal edge as illustrated, or may be totally separable so as to be movable into protective position horizontally along the surface of basin side wall 15. A suitable plug 44 and socket 45 engagement may be provided to secure the abutting edges of the plate halves together with the holes 42, 43 disposed about the spacers. Inadvertent removal of the plate 40, 41 from its deployed position may be prevented by adhesive backing on the plate, by friction engagement between one or more spacers and one or more holes, or other suitable means.

FIG. 11 illustrates another protective device for the drape and takes the form of a strip 50 of fabric adapted to be supported on basin flange 17 and be suspended down along side wall 15 to overlie the three spacers 21 in a group. The fabric of strip 50 is suitably thick to effectively blunt the abruptness of the annular edges of spacers 21. Attachment of strip 50 to flange 17 is accomplished by means of a Velcro connector, or the like, disposed on the upper end of the rear surface of strip 50 and on flange 17. Alternatively, adhesive may be used to permanently secure strip 50 to flange 17, although the Velcro-type engagement permits easy removal of the protective device should that be desired.

The protective member embodiment illustrated in FIG. 13 takes the form of a plate 53 similar to plate 23 (FIG. 3) except that no through holes are defined therein. Instead, a channel 54 is defined vertically in the rear surface of the plate. The width of channel 54 is selected to be wider than the diameter of spacers 21 while the length of the channel is sufficient to permit all of the spacers of a group of spacers to be simultaneously received in the channel. Channel 54 may extend in length from the bottom edge of the plate to a location below the top edge, as illustrated, whereby the plate is positioned by moving it downwardly over the three aligned spacers until the end of the channel near the top of the plate engages the top of the upper spacer in the group. The plate is then pressed toward basin side wall 15 so as to be secured thereto via adhesive backing 55, or the like, disposed on the unrecessed portion of the rear surface of the plate. Since the spacers are entirely hidden in channel 54, no spacer edges are exposed to drape 30. It will also be appreciated that channel 54 can extend the entire length of the rear surface of plate 53.

A further alternative protective plate 57 is illustrated in FIG. 14. In this embodiment the plate has a channel 58 defined in and extending the entire length of the rear surface of the plate. Channel 58 is similar to channel 54 except that centered in channel 58 is an annular sleeve 59 having an inner diameter adapted to permit the sleeve to receive the central spacer 21 in a group of three spacers, the inner diameter being selected to provide a force-fit engagement with that spacer. With the central spacer thusly positioned, the two end spacers of the group reside in channel 58 and all of the spacers are thusly protected. The unrecessed portion of the rear surface of the plate may be coated with adhesive, or the like, or the force-fit between sleeve 59 and its spacers may be used alone to secure plate 57 in place.

FIG. 16 illustrates a further embodiment of a protective member of the present invention. In this embodiment each individual spacer 21, rather than a spacer group, is individually protected. Each spacer is received in a recess 61 in the rear surface of a respective generally cylindrical protective button or cap 60. The transition between the front surface and cylindrical surface of cap 60 is rounded rather than being abrupt to thereby protect against tearing or snagging of drape 30. Cap 60 is preferably made of elastomeric material such as rubber or plastic and has the recess in its rear surface configured to engage spacer 21 in force-fit relation. Alternatively, cap 60 may be secured to spacer 21 and/or basin side wall 15 with adhesive. This embodiment permits either individual spacers within a group or the sole spacer on bottom wall 13 to be protected by protective device 60 (see FIG. 6).

Another form of protective member secured to individual spacers is illustrated in FIG. 17 and is configured as an O-ring or similar annular gasket 65 having an inner diameter adapted to be force-fit onto the cylindrical periphery of a respective spacer 21. Gasket 65 is made of elastomeric material and has a thickness greater than the axial length of spacer 21 so that the abrupt annular edge of the spacer is recessed relative to the gasket.

Referring to FIGS. 12 and 15, the method according to the present invention involves, as a first step, covering the spacers or studs with a protective device of the present invention to protect the drape receptacle 30. In most instances this step will be performed only once since the protective members will be permanently installed over the spacers. However, it may be desirable that the protective devices be removed occasionally, in which case the protective step is performed again before a slush producing procedure is to be initiated. Once the abrupt spacer edges are rendered inaccessible, drape 30 is placed over the top of the cabinet and made to conform to the basin interior over the various protective members. In most instances the drape will be large enough to extend over the sides of the cabinet. After drape 30 has been formed as a receptacle in the basin, sterile liquid may be introduced therein in the desired amount. Upon activation of the refrigeration unit, the basin is cooled by the evaporator through the basin and the drape to cause the liquid to congeal along the sides of the drape receptacle. The sides of the drape may then be lifted and manipulated to break up congealed liquid adhering thereto. A whisk 70 may be used to stir the congealed material in the drape receptacle to achieve a surgical slush of desired consistency in the receptacle interior. Upon achieving the desired consistency the refrigeration unit may be turned off and the drape receptacle removed from basin 11. After use the disposable drape may be discarded.

As noted above, the plate configurations for the protective member of the present invention may be made of any suitable material such as metal, plastic, or the like, or any combination thereof. In particular, the plate may have a relatively soft silicon backing formed on a somewhat harder metal or plastic plate. If the plate or other protective device is made of a material having a different thermal coefficient of expansion than spacers 21, it may not be possible to rely on force-fit engagement between the protective member and the spacer in securing the protected member to the spacers. In such cases the use of adhesive may be more appropriate. It should also be noted that the holes in the various protective plates need not necessarily be circular or even the same general shape as the periphery of the spacers. The important point is that the abrupt spacer edges are rendered inaccessible to the drape 30 when the drape is made to conform to the basin interior.

From the foregoing description it will be appreciated that the invention makes available a novel method and apparatus for permitting the system disclosed in the aforementioned Keyes et al patent to be used in conjunction with a drape for directly receiving sterile liquid and collecting sterile surgical slush rather than utilizing a separate basin and thermal transfer liquid disposed between the basins.

Having described preferred embodiments of a new and improved method and apparatus for producing sterile surgical slush in accordance with the present invention, it is believed that other modifications, variations and changes will be suggested to persons skilled in the art after having access to the teachings set forth herein. It is therefore to be understood that all such variations, modifications and changes are believed to fall within the scope of the present invention as defined by the appended claims.

What is claimed is:

1. A method for use with apparatus for producing sterile slush from a sterile surgical liquid, the apparatus comprising a heat transfer basin, a refrigeration mechanism including an evaporator in heat transfer relation to the heat transfer basin, and spacers secured to the basin and projecting into the basin interior at plural spaced locations, each spacer including at least one exposed abrupt edge defining the intersection between surfaces of the spacer, said method comprising the steps of:
   (a) protecting each of the exposed spacer edges against direct contact from the basin interior;
   (b) covering the interior of the basin with a sterilized drape by directly contacting the basin with a first side of said drape and conforming the drape substantially to the shape of the basin interior, whereby a second side of the drape is exposed in the basin interior and defines a liquid receptacle, said drape comprising a sheet of material that is impervious to the sterile liquid and sufficiently thin to permit thermal energy transfer between the basin and fluid contacting the second side of said drape;
   (c) introducing a quantity of sterile liquid directly into the drape receptacle; and
   (d) operating the refrigeration mechanism to cause the introduced sterile liquid to congeal against the second surface of the drape;
   wherein by step (a) prevents tearing and snagging of said drape by the spacer edges.

2. The method of claim 1 further comprising the step of:
   (e) stirring the congealed liquid during step (d) to produce a quantity of sterile slush at a desired consistency;
   wherein step (a) prevents tearing and snagging of said drape by the spacer edges during steps (b), (c), (d) and (e).

3. The method apparatus of claim 2 further comprising the step of:
   (f) manipulating said drape to remove congealed liquid therefrom;
   wherein step (a) prevents tearing and snagging of said drape by the spacer edges during each of steps (b), (c), (d), (e) and (f).

4. The method apparatus of claim 1 further comprising the step of:
   (e) manipulating said drape to remove congealed liquid therefrom;
   wherein step (a) prevents tearing and snagging of said drape receptacle by the spacer edges during each of steps (b), (c), (d) and (e).

5. The method apparatus of claim 1 wherein step (a) comprises completely covering all surfaces of said spacers from exposure to the basin interior.

6. The method apparatus of claim 1 wherein step (a) comprises completely covering each exposed edge of the spacers.

7. The method apparatus of claim 1 wherein step (a) comprises securing a protective member adjacent each spacer to effectively recess the exposed spacer edge relative to the protective member while exposing at least one surface of the spacer to the basin interior, wherein the protective member has no exposed abrupt edges that can tear or snag said drape.

8. The method apparatus of claim 1 wherein step (a) comprises force-fitting individual protective members about the peripheries of respective spacers such that the protective members project inwardly of the basin beyond the exposed spacer edge, whereby the protective members prevent said drape from contacting exposed spacer edges.

9. An apparatus for use in a system for producing sterile surgical slush from a sterile liquid, the system being of the type having a heat transfer basin, a refrigeration mechanism including an evaporator in heat transfer relation to the basin, and spacers secured to the basin and projecting into the basin interior, each spacer including at least one exposed edge defining an intersection between two surfaces of that spacer, said apparatus comprising:
   a sterilized drape of material impervious to the sterile liquid and sized to cover and directly contact the basin, said drape also being sufficiently soft to conform to the interior shape of the basin whereby the sterile liquid can be directly contained by said drape serving as a receptacle in the basin; and
   protective means disposed between the basin and said drape for preventing contact between said drape and the exposed edges of each of the spacers to thereby prevent tearing or snagging of said drape by the spacer edges.

10. The apparatus of claim 9 wherein said protective means comprises means surrounding each spacer and projecting into the basin interior beyond each spacer edge.

11. The apparatus of claim 9 wherein each spacer is a short cylindrical stub and the exposed edge is annular, and wherein said protective means comprises a plurality of annular members, one for each of the spacers, each annular member being adapted to circumferentially engage a respective spacer while projecting in thickness into the basin interior beyond the location of the spacer edge.

12. The apparatus of claim 9 wherein each spacer is a short cylindrical stub and the exposed edge is annular, and wherein said protective means comprises a plurality of caps, one cap for each spacer, each cap being adapted to be secured in complete covering relation to a respective spacer.

13. The apparatus of claim 9 wherein the spacers are arranged in plural groups projecting from the side of the basin, each group comprising a plurality of vertically aligned stub-like projections from the basin side, and wherein said protective means comprises a plurality of plates, one plate for each group, each plate adapted to be secured relative to the basin side in surrounding relation to all of the spacers in a respective group, said plate having sufficient thickness to project into the basin interior beyond the spacers and being devoid of abrupt edges and corners that could tear or snag said drape.

14. The apparatus of claim 13 wherein said plate includes a plurality of through holes, one through hole for each spacer in said respective group, the through holes being configured to substantially match the peripheries of the spacers.

15. The apparatus of claim 14 wherein at least one of said through holes is configured to engage a respective spacer in force fit relation.

16. The apparatus of claim 14 wherein said plate comprises two plate halves, each half including one-half of each of said through holes, said plate halves being adapted to be secured to one another relative to said basin from opposite sides of said spacers.

17. The apparatus of claim 13 wherein said plate has a channel defined to a predetermined depth in a rear surface of the plate, the channel being configured to receive all of the spacers in said respect of group of spacers.

18. The apparatus of claim 9 wherein said protective means comprises at least one strip of fabric secured to said basin and overlying said spacers, said strip of fabric being sufficiently thick to effectively blunt the exposed edges of said spacers.

* * * * *